(12) United States Patent
Dorwal et al.

(10) Patent No.: US 8,987,525 B2
(45) Date of Patent: Mar. 24, 2015

(54) PROCESS FOR THE PREPARATION OF POLYHYDROXYSTILBENE COMPOUNDS BY DEPROTECTION OF THE CORRESPONDING ETHERS

(71) Applicants: Harish Niranjanlal Dorwal, Hyderabad (IN); Sandirane Sabapathy, Hyderabad (IN); Seeta Raman Gorantla, Hyderabad (IN); Satyanarayana Chava, Hyderabad (IN)

(72) Inventors: Harish Niranjanlal Dorwal, Hyderabad (IN); Sandirane Sabapathy, Hyderabad (IN); Seeta Raman Gorantla, Hyderabad (IN); Satyanarayana Chava, Hyderabad (IN)

(73) Assignee: Laurus Labs Private Ltd., Hyderabad (IN)

( * ) Notice: Subject to any disclaimer, the term of this patent is extended or adjusted under 35 U.S.C. 154(b) by 0 days.

(21) Appl. No.: 14/353,869

(22) PCT Filed: Nov. 30, 2012

(86) PCT No.: PCT/IN2012/000783
§ 371 (c)(1),
(2) Date: Apr. 24, 2014

(87) PCT Pub. No.: WO2013/080226
PCT Pub. Date: Jun. 6, 2013

(65) Prior Publication Data
US 2015/0031921 A1    Jan. 29, 2015

(30) Foreign Application Priority Data

Dec. 1, 2011    (IN) .......................... 4162/CHE/2011

(51) Int. Cl.
*C07C 37/055*    (2006.01)

(52) U.S. Cl.
CPC ................................ *C07C 37/055* (2013.01)
USPC .......................................... 568/729

(58) Field of Classification Search
None
See application file for complete search history.

(56) References Cited

U.S. PATENT DOCUMENTS 7,253,324 B1 *    8/2007    Majeed et al. ................ 568/805

FOREIGN PATENT DOCUMENTS

WO    WO/2008/091379    7/2008

* cited by examiner

*Primary Examiner* — Brian J Davis
(74) *Attorney, Agent, or Firm* — Blank Rome LLP

(57) ABSTRACT

A process for the preparation of polyhydroxystilbene compounds (particularly resveratrol, oxyresveratrol, piceatannol, gnetol and the like) by deprotection of the corresponding ethers using aluminum halide and a secondary amine is provided.

20 Claims, No Drawings

PROCESS FOR THE PREPARATION OF POLYHYDROXYSTILBENE COMPOUNDS BY DEPROTECTION OF THE CORRESPONDING ETHERS

PRIORITY

This application is a U.S. National Phase of PCT/IB2012/001444, filed Jul. 26, 2012, which claims the benefit under Indian Provisional Application No. 4162/CHE/2011, filed Dec. 1, 2011, the content of each of which is incorporated by reference herein.

FIELD OF THE INVENTION

The present invention generally relates to a process for the preparation of polyhydroxystilbene compounds by deprotection of the corresponding ethers. The invention particularly relates to a process for the preparation of resveratrol and its analogues, and to pharmaceutical compositions containing the same.

BACKGROUND OF THE INVENTION

Compounds containing aromatic hydroxyl functions such as polyhydroxy stilbenes are found in various plants and which have great importance as they exhibit excellent therapeutic properties such as use as antioxidants, platelet antiaggregants, anti-inflammatory or vasodilator, or as cell proliferative inhibitors.

The polyhydroxy stilbenes include Resveratrol ((E)-5-(4-hydroxystyryl)benzene-1,3-diol), Oxy resveratrol (4-[(E)-2-(3,5-Dihydroxyphenyl)ethenyl]benzene-1,3-diol), Piceatannol (5-[(E)-2-(3',4'-dihydroxyphenyl)vinyl]benzene-1,3-diol) and Gnetol (2-[(1E)-2-(3,5-Dihydroxyphenyl)ethenyl]-1,3-benzenediol) of formulae:

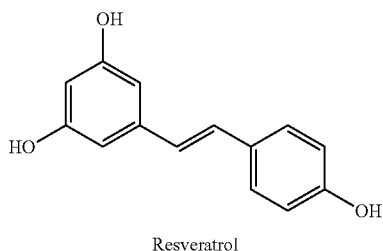

Resveratrol

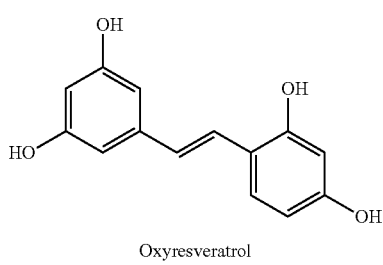

Oxyresveratrol

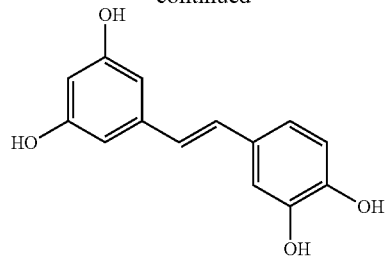

Piceatannol

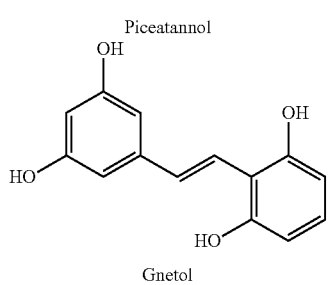

Gnetol

In the synthesis of polyhydroxy stilbenes, the phenolic groups such as phenolic —OH must be protected in the form of ether derivatives in order to decrease the acidity of the phenolic hydrogens. The phenolic —OH groups can be protected by different protecting groups selected from methyl, methylene, isopropyl, t-butyl, acyl, benzyl or tetrahydropyranyl (THP) and the like. Once the phenolic group is protected as an ether, reactions could be performed on the molecule; finally the ether must be deprotected to release the parent phenolic —OH. Several deprotection methods have been described in the literature; however they suffer from one disadvantage or another.

Several methods have been described for deprotection of phenolic ethers. For example, phenolic methyl ethers have deprotected to remove the methyl moiety using hydrogen halide such as hydrogen chloride or hydrogen bromide under highly acidic conditions; highly colored products formed in these reactions. In addition the phenolic compounds react further with the halogen compounds used thus setting a major drawback on this route. In the case of benzyl ethers, deprotection is carried out by catalytic hydrogenation, which results, in the specific case stilbene derivatives; the carbon-carbon double bond may get hydrogenated.

U.S. Pat. No. 6,844,471, U.S. Pat. No. 7,253,324 and Tetrahedron Lett. 32, 10, 1991, 1321-24 discloses Lewis acids-aromatic amine for deprotection of phenolic ethers such as benzyl, allyl or alkyl ethers, particularly in the preparation of resveratrol and piceatannol. However, the aromatic amines used are expensive, highly toxic and difficult to remove.

PCT publication No. WO 2009/043761 ("the '761 publication") discloses a process for the synthesis of stilbene derivatives by deprotection of corresponding ethers using aluminium chloride-aliphatic tertiary amine such as triethylamine or tributylamine in chlorobenzene.

Other Lewis acids such as boron tribromide/boron trichloride etc have been disclosed in U.S Patent publication No. 2005/240062, Tetrahedron Lett., 44, 1 (2003), 193-198 and Tetrahedron, 59 (2003), 3315-3321 for deprotection of phenolic methyl, benzyl or isopropyl ethers. In these Lewis acids very low temperatures are required to perform the reaction, which in turn inconvenience of performing such reactions in larger commercial scale. Moreover, boron tribromide/boron trichloride, are expensive reagents which are unsafe to use industrially.

CN Patent No. 1663939 discloses a demethylation process of phenolic methyl ethers for the preparation of resveratrol by using aluminium chloride-pyridine system at temperature of 165° C. to 170° C. The use of toxic pyridine solvent and reaction at higher temperatures are not appropriate selection for industrial large scale process.

Accordingly, there remains a need for an alternative process for preparation of polyhydroxy stilbenes, particularly for the purpose of the synthesis of resveratrol and its analogues, which is simple and cost effective.

The present invention provides a process for the preparation of polyhydroxy stilbenes by using simple and commercially available deprotecting agents such as Lewis acid-Secondary amines that are away from the aforementioned difficulties. The process of the present invention can be practiced on an industrial scale, and also can be carried out without sacrifice of overall yield.

SUMMARY OF THE INVENTION

The present invention encompasses a process for the preparation of polyhydroxy stilbenes, particularly resveratrol and its analogues with high product yield and quality.

In accordance with one embodiment, the present invention provides a process for preparation of polyhydroxy stilbenes of Formula I or its isomers thereof:

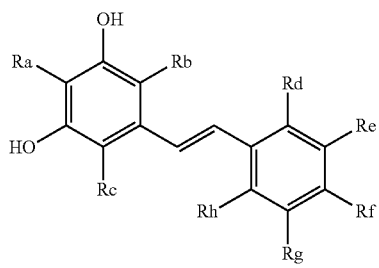

Formula I in which:

Rd, Rf, Rg and Rh represents hydrogen or a OH group;

Ra, Rb, Rc and Re independently represents a hydrogen or optionally substituted substituent chosen from: a halogen; a nitro group; a linear or branched $C_1$-$C_4$ alkyl group; a linear or branched $C_2$-$C_6$ alkenyl group; a $C_3$-$C_{10}$ cycloalkyl group; a cycloalkylalkyl group in which the cycloalkyl and alkyl groups are as defined above; an aryl group; or an aralkyl group;

comprising: deprotection of a compound of Formula II or its isomers thereof:

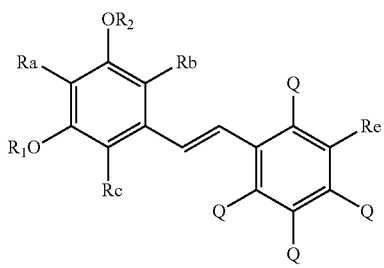

Formula II in which:

Ra, Rb, Rc and Re are defined as above;

Q represents hydrogen or an ORi group and $R_1$, $R_2$ and Ri independently represents a linear or branched $C_1$-$C_4$ alkyl group; a C(=O)Rj, in which Rj represents a linear or branched $C_1$-$C_4$ alkyl group; or an aralkyl group, wherein aryl in the aralkyl group optionally substituted by one or more $C_1$-$C_4$ alkoxy or halogen groups; wherein the deprotection is carried out with use of an aluminium halide and a secondary amine.

In accordance with a second embodiment, the present invention provides a process for preparation of polyhydroxy stilbenes of Formula I or its isomers thereof:

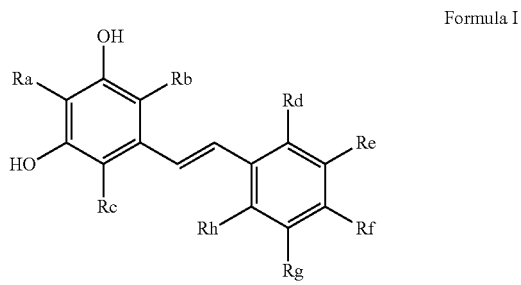

Formula I in which:

Rd, Rf, Rg and Rh represents hydrogen or a OH group;

Ra, Rb, Rc and Re independently represents a hydrogen or optionally substituted substituent chosen from: a halogen; a nitro group; a linear or branched $C_1$-$C_4$ alkyl group; a linear or branched $C_2$-$C_6$ alkenyl group; a $C_3$-$C_{10}$ cycloalkyl group; a cycloalkylalkyl group in which the cycloalkyl and alkyl groups are as defined above; an aryl group; or an aralkyl group;

comprising: deprotection of a compound of Formula II or its isomers thereof:

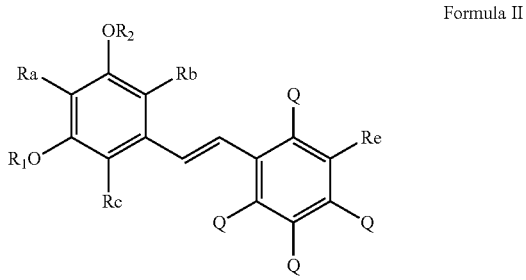

Formula II in which:

Ra, Rb, Rc and Re are defined as above;

Q represents hydrogen or an ORi group and $R_1$, $R_2$ and Ri independently represents a linear or branched $C_1$-$C_4$ alkyl group; a C(=O)Rj, in which Rj represents a linear or branched $C_1$-$C_4$ alkyl group; or an aralkyl group, wherein aryl in the aralkyl group optionally substituted by one or more $C_1$-$C_4$ alkoxy or halogen groups;

wherein the deprotection is carried out with use of an aluminium halide and a secondary amine;

wherein the secondary amine has the following Formula:

$(R)_2NH$, in which R represents a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group or an aralkyl group.

In accordance with a third embodiment, the present invention provides a process for preparation of polyhydroxy stilbenes of Formula IA or its isomers thereof:

Formula IA

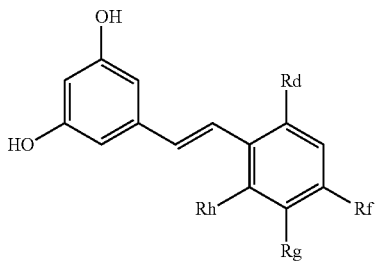

in which: Rd, Rf, Rg and Rh represents hydrogen or a OH group;
comprising: deprotection of a compound of Formula IIA or its isomers thereof:

Formula IIA

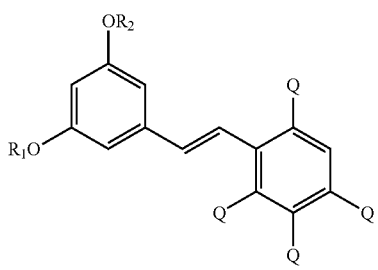

in which:
Q represents hydrogen or an ORi group and $R_1$, $R_2$ and Ri independently represents a linear or branched $C_1$-$C_4$ alkyl group; a C(=O)Rj, in which Rj represents a linear or branched $C_1$-$C_4$ alkyl group; or an aralkyl group, wherein aryl in the aralkyl group optionally substituted by one or more $C_1$-$C_4$ alkoxy or halogen groups; wherein the deprotection is carried out with use of an aluminium halide and a secondary amine of Formula $(R)_2NH$, in which R represents a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group or an aralkyl group.

In accordance with a fourth embodiment, the present invention provides a process for preparation of resveratrol or its isomers thereof:

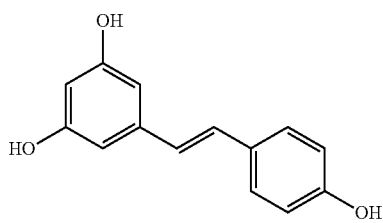 [SMILES: Oc1ccc(/C=C/c2cc(O)cc(O)c2)cc1]

comprising: deprotection of a resveratrol ether compound or its isomers thereof:

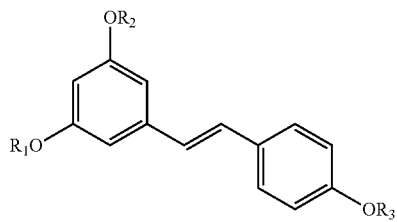

in which:
$R_1$, $R_2$ and $R_3$ independently represents a linear or branched $C_1$-$C_4$ alkyl group; a C(=O)Rj, in which Rj represents a linear or branched $C_1$-$C_4$ alkyl group; or an aralkyl group, wherein aryl in the aralkyl group optionally substituted by one or more $C_1$-$C_4$ alkoxy or halogen groups; wherein the deprotection is carried out with use of an aluminium halide and a secondary amine of Formula $(R)_2NH$, in which R represents a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group or an aralkyl group.

In accordance with a fifth embodiment, the present invention provides a pharmaceutical composition comprising polyhydroxy stilbens prepared by the process of the present invention.

DETAILED DESCRIPTION OF THE INVENTION

The present invention encompasses a process for the preparation of polyhydroxy stilbenes by deprotection of corresponding ethers.

In particular, the present invention provides a process for preparation of resveratrol and its analogues with high product yield and quality.

In one embodiment, the present invention provides a process for preparation of polyhydroxy stilbenes of Formula I or its isomers thereof:

Formula I

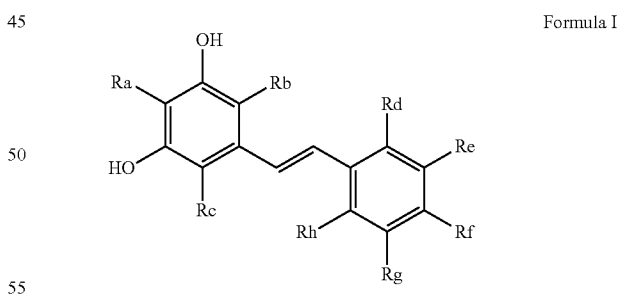

in which:
Rd, Rf, Rg and Rh represents hydrogen or a OH group;
Ra, Rb, Rc and Re independently represents a hydrogen or optionally substituted substituent chosen from: a halogen; a nitro group; a linear or branched $C_1$-$C_4$ alkyl group; a linear or branched $C_2$-$C_6$ alkenyl group; a $C_3$-$C_{10}$ cycloalkyl group; a cycloalkylalkyl group in which the cycloalkyl and alkyl groups are as defined above; an aryl group; or an aralkyl group;
comprising: deprotection of a compound of Formula II or its isomers thereof:

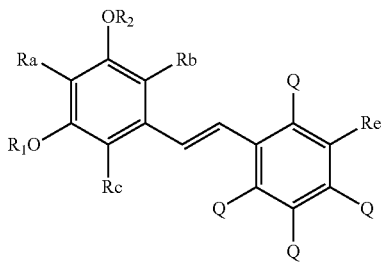

Formula II in which:

Ra, Rb, Rc and Re are defined as above;

Q represents hydrogen or an ORi group and $R_1$, $R_2$ and Ri independently represents a linear or branched $C_1$-$C_4$ alkyl group; a C(=O)Rj, in which Rj represents a linear or branched $C_1$-$C_4$ alkyl group; or an aralkyl group, wherein aryl in the aralkyl group optionally substituted by one or more $C_1$-$C_4$ alkoxy or halogen groups;

wherein the deprotection is carried out with use of an aluminium halide and a secondary amine of Formula $(R)_2NH$, in which R represents a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group or an aralkyl group.

The halogen includes chlorine, bromine, fluorine or iodine;

the linear or branched $C_1$-$C_4$ alkyl group includes, but is not limited to methyl, ethyl, propyl, isopropyl, butyl, isobutyl, sec-butyl, or tert-butyl group and the like;

the linear or branched $C_2$-$C_6$ alkenyl group includes, but is not limited to an ethenyl or vinyl, propenyl or allyl, 1-propenyl, n-butenyl, isobutenyl, 3-methylbut-2-enyl, n-pentenyl or hexenyl group and the like;

the a $C_1$-$C_6$ alkanol includes, but is not limited to methanol, ethanol, propanol, butanol, and the like;

the $C_3$-$C_{10}$ cycloalkyl group includes, but is not limited to cyclopropyl, cyclohexyl and the like;

the cycloalkylalkyl group includes, but is not limited to cyclopropylmethyl, cyclobutylmethyl, cyclopentylmethyl, cyclohexylmethyl, cycloheptylmethyl, cyclopropylethyl or cyclohexylethyl group and the like;

the aryl group includes, but is not limited to phenyl, naphthyl, indenyl or anthracenyl and the like;

the aralkyl group includes, but is not limited to benzyl, 1-phenylethyl, naphthalenylmethyl or 1-naphthalenylethyl and the like;

the linear or branched alkyl group includes, but is not limited to methyl, ethyl, n-propyl, isopropyl, butyl, isobutyl, sec-butyl, tert-butyl; pentyl, hexyl, heptyl, octyl, ethylhexyl and the like;

the $C_1$-$C_4$ alkoxy includes, but is not limited to methoxy, ethoxy, propoxy or butoxy and the like.

In a preferred embodiment of the present invention, the polyhydroxy stilbenes of Formula I or its isomers thereof;

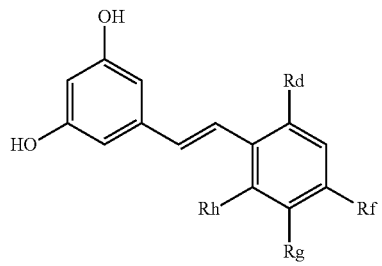

Formula I in which Rd, Rf, Rg and Rh being as defined above; prepared by deprotection of a compound of Formula II or its isomers thereof;

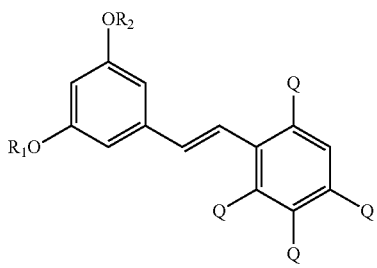

Formula II in which Q represents hydrogen or an ORi group; and $R_1$, $R_2$ and Ri independently represents a linear or branched $C_1$-$C_4$ alkyl group such as methyl, ethyl or t-butyl and a $C_7$-$C_{16}$ aralkyl group such as benzyl group.

In another preferred embodiment of the present invention applies the polyhydroxy stilbenes of Formula I or its isomers thereof

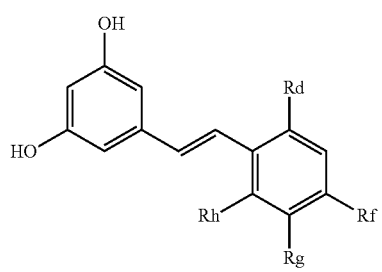

Formula I in which Ra, Rb, Rc and Re independently represents hydrogen and Rd, Rf, Rg and Rh being as defined above; prepared by deprotection of a compound of Formula II or its isomers thereof

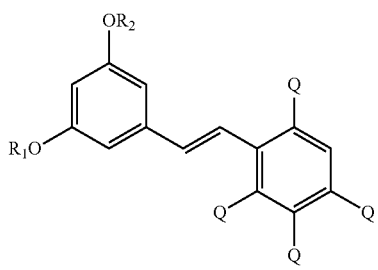

Formula II in which Q represents hydrogen or an ORi group; and $R_1$, $R_2$ and Ri independently represents a methyl group.

In another embodiment of the invention, the aluminium halide is selected from the group consisting of aluminium chloride, aluminium bromide, aluminium iodide and the like and mixtures thereof; preferably aluminium chloride.

In another preferred embodiment of the invention, the secondary amine Formula $(R)_2NH$ may be selected from the group consisting of diethylamine, diisopropyl amine, di-n-propylamine, diisobutylamine, diallylamine, allylmethyl amine, diphenylamine, dibenzylamine, benzylethyl amine, methylbenzyl amine, dicyclohexylamine, N-t-butyl cyclohexylamine, N-isobutyl cyclohexylamine, di(2-ethylhexyl) amine, dicyclohexylmethyl amine and the like; preferably diisopropyl amine, diethylamine, di-n-propylamine, diisobutylamine, dicyclohexylamine, di(2-ethylhexyl)amine.

The molar ratio of the aluminium halide:secondary amine used in the process according to the invention may vary between 1:1 and 1:4; preferably 1:1 to 1:2, more preferably 1:1 to 1:1.5.

The aluminium halide and the secondary amine can be introduced in any order, for example the aluminium halide is added to the secondary amine and then the compound of Formula II is introduced or the compound of formula II is added to the amine and then the aluminium halide is introduced. The sequence of addition of aluminium halide and/or secondary amine is not particularly critical. Alternatively, the aluminium halide-secondary amine is formed beforehand and is optionally isolated, before the introduction of the compound of Formula II; preferably first adding the aluminium halide and secondary amine and then Formula II is introduced.

The deprotection of the foregoing process may be carried out at a temperature of about ambient temperature to about reflux temperature. Preferably the reaction temperature is about 35° C. to about 140° C., more preferably at about 80° to about 130° C., most preferably at about 110° C. to about 120° C.

The reaction can be carried out without use of solvent or with the use of solvent. Preferably the reaction is carried out in a solvent, wherein the solvent include but is not limited to halogenated hydrocarbons selected from the group consisting of dichloromethane, dichloroethane, chloroform and the like; aromatic hydrocarbons selected from the group consisting of toluene, xylene, chlorobenzene, 1,2-dichlorobenzene and the like; ethers such as diphenyl ether and the like; preferably toluene, xylene, chlorobenzene; more preferably toluene.

In another embodiment, the present invention provides a process for preparation of resveratrol or its isomers thereof:

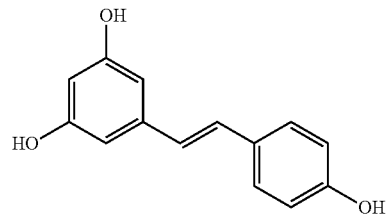 [SMILES: Oc1ccc(/C=C/c2cc(O)cc(O)c2)cc1]

comprising: deprotection of a resveratrol ether compound or its isomers thereof:

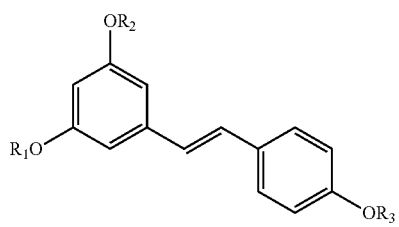

in which:
$R_1$, $R_2$ and $R_3$ independently represents a linear or branched $C_1$-$C_4$ alkyl group; a $C(=O)Rj$, in which Rj represents a linear or branched $C_1$-$C_4$ alkyl group; or an aralkyl group, wherein aryl in the aralkyl group optionally substituted by one or more $C_1$-$C_4$ alkoxy or halogen groups; preferably $R_1$, $R_2$ and $R_3$ is methyl group;
wherein the deprotection is carried out with use of an aluminium halide and a secondary amine of Formula $(R)_2NH$, in which R represents a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group or an aralkyl group; preferably the secondary amine is selected from the group consisting of diethylamine, diisopropyl amine, di-n-propylamine, diisobutylamine, diallylamine, allylmethyl amine, diphenylamine, dibenzylamine, benzylethyl amine, methylbenzyl amine, dicyclohexylamine, N-t-butyl cyclohexylamine, N-isobutyl cyclohexylamine, di(2-ethylhexyl)amine, dicyclohexylmethyl amine, and the like; more preferably diisopropyl amine, diethylamine, di-n-propylamine; most preferably diisopropyl amine.

In another embodiment, crude resveratrol thus obtained may be purified. For example, resveratrol thus obtained may be dissolved in water in presence of base such as sodium hydroxide and washed with a water immiscible organic solvent. The aqueous layer may be separated and precipitated the product by treatment with an acid such as hydrochloric acid.

The water immiscible organic solvent includes, but is not limited to esters such as methyl acetate, ethyl acetate, isopropyl acetate and the like; aromatic hydrocarbons include, but are not limited to toluene, xylene and the like; halogenated hydrocarbons include, but are not limited to dichloromethane, dichloroethane, chloroform and the like; preferably the water immiscible organic solvent is ethyl acetate, toluene, dichloromethane; more preferably toluene.

In another embodiment, alternatively crude resveratrol thus obtained may be purified by dissolving crude resveratrol in suitable water immiscible organic solvent defined just as above and washed with an acid such as hydrochloric acid. The resultant water immiscible organic solvent layer may be removed and isolated the pure resveratrol. The isolation may be carried out in any known manner, for example solvent crystallization in presence of a suitable organic solvent.

In another embodiment, the thus obtained resveratrol may be further purified in a mixture of an organic solvent and water by dissolving the resveratrol in an organic solvent such as C1-4 alcohols selected from methanol, ethanol, isopropanol, butanol, t-butanol and the like; water and mixtures thereof, with methanol or isopropanol being preferred. The solvent may be heated to obtain a solution at a temperature of from about ambient temperature to about reflux temperature. Pure Resveratrol may be precipitated by either cooling the solution or adding anti solvent (water) to the resveratrol solution and then the solution may be cooled at a temperature from about 20° C. or less such that the pure resveratrol can be isolated by conventional techniques.

The following examples are provided to enable one skilled in the art to practice the invention and are merely illustrative of the invention. The examples should not be read as limiting the scope of the invention as defined in the claims.

EXAMPLES

Example 1

Preparation of Resveratrol Using Diisopropyl Amine: Aluminium Chloride

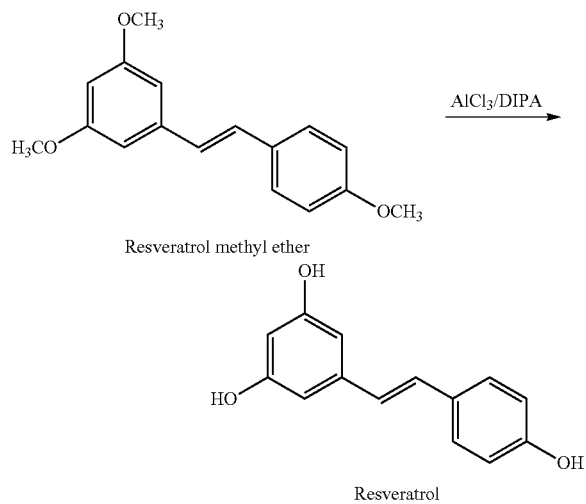

To a clean 3-necked 2 L round bottom flask equipped with a mechanical stirrer, thermometer socket and addition funnel was charged di-isopropyl amine (168.5 gms) at 25° to 35° C. To the solution aluminium chloride (222 gms) was added in lots at 25° C. to 35° C. and heated to 110° C. Reaction solution was stirred for 30 minutes and then resveratrol methyl ether solution (75 gms of resveratrol methyl ether in 300 ml of toluene) was added at 100° C. to 110° C. Reaction mass was stirred for 4 hours at 110° C. to 120° C. and then allowed to cool to 80° C. to 90° C. The reaction mass was quenched into chilled water (1050 ml) at below 45° C. and stirred for 30 minutes at same temperature. Precipitated material was filtered and washed with water (150 ml). The wet product (160 gms) was taken into a 3-necked 2 L round bottom flask and water (1125 ml) was charged at 25° C. to 35° C. To the mass sodium hydroxide solution (188 ml; 33.5 gms of sodium hydroxide dissolved in 188 ml water) was added and then reaction solution was washed with toluene (2×195 ml). The aqueous layer was separated out and pH was adjusted to 2 with Con HCl (71.25 ml) at 25° to 30° C. and stirred for 60 minutes at same temperature. Precipitated product was filtered and washed with water (150 ml) and the wet cake was slurred in water (750 ml) at temperature 80° to 85° C. followed by filtered and dried at 75° to 85° C. to provide the title compound.

Yield: 47.5 gms.
HPLC purity: 99.49%

Example 2

Purification of Resveratrol Using IPA+Water

To a clean 3-necked 2 L round bottom flask equipped with a mechanical stirrer, thermometer socket was charged IPA (320 ml) and crude resveratrol (40 gms; obtained from Example-1) at 25° to 35° C. The reaction mass was heated to 75° to 80° C. and then allowed to cool to 65° to 75° C. The clear solution was treated with charcoal at 70° to 80° C. for 15 minutes and the charcoal was separated out. To the resultant reaction solution water (900 ml) was added at 65° to 75° C. and stirred for 30 minutes at 70° to 75° C. The resultant solution was allowed to cool to 20° C. and stirred for 60 minutes at 20° to 25° C. Precipitated solids was filtered and washed with water (40 ml). The wet product was dried at 85° C. to 90° C. for 6 hours to provide the title compound.

Yield: 33.7 gms.
HPLC purity: 99.85%

Example 3

Purification of Resveratrol Using Ethanol+Water

To a clean 3-necked 2 L round bottom flask equipped with a mechanical stirrer, thermometer socket was charged ethanol (178 ml), water (27 ml) and resveratrol (30 gms) at 25° to 35° C. The reaction mass was heated to 70° to 75° C. and stirred for 60 minutes at same temperature. The reaction solution was allowed to cool to 65° to 75° C. and the clear solution was treated with charcoal at 65° to 75° C. for 30 minutes and the charcoal was separated out. To the resultant reaction solution hot water (640 ml) was added at 70° to 75° C. and then allowed to cool to 40° C. to 45° C. and stirred for 60 minutes at same temperature. The resultant solution was allowed to further cool to 10° C. to 15° C. and stirred for 60 minutes at same temperature. Precipitated solids was filtered and slurred with water (150 ml) at 70° to 75° C. The slurry was allowed to cool to 40° C. to 45° C. and filtered. The wet product was dried at 85° C. to 90° C. for 6 hours to provide the title compound.

Yield: 27.2 gms.
HPLC purity: 99.88%

Example 4

Preparation of Resveratrol Using Diisopropyl Amine: Aluminium Chloride

To a clean 3-necked 2 L round bottom flask equipped with a mechanical stirrer, thermometer socket and addition funnel, aluminium chloride (148 gms) and di-isopropyl amine (112 gms) were charged at 25° C. to 35° C. The reaction mass was heated to 110° C. to 120° C. and stirred, for 30 minutes and then resveratrol methyl ether solution (50 gms of resveratrol methyl ether in 200 ml of toluene) was added at 110° C. to 120° C. Reaction mass was stirred for 4 hours at 110° C. to 120° C. and then allowed cool to 80° C. to 90° C. To the resultant mass Toluene (100 ml) was charged and then quenched the reaction mass into chilled water (700 ml) and stirred for 30 minutes at 25° C. to 35° C. Precipitated material was filtered and washed with water (50 ml). The wet product was slurred in hot water at 40° C. to 45° C. for 30 minutes and filtered. The wet product was dried at 70° C. to 80° C. for 4 hours under vacuum to provide the title compound as crude. The crude compound was dissolved in ethyl acetate (330 ml) at 40° C. to 45° C. and washed with aqueous HCl solution (17 ml of con HCl+65 ml of water) and then with water (65 ml). Layers were separated and distilled out the ethyl acetate under vacuum to obtain residue. The resultant residue was dissolved in methanol (330 ml) at 40° C. to 45° C. and then water (1000 ml) was added at 25° C. to 35° C. Precipitated solids was filtered and washed with 10% methanol-water (35 ml). The wet product was dried at 70° C. to 80° C. under vacuum for 4 hours to provide the title compound.

Yield: 29 gms
HPLC Purity: 99.66%

Example 5

Preparation of Resveratrol Using Diethyl Amine: Aluminium Chloride

To a clean 3-necked 2 L round bottom flask equipped with a mechanical stirrer, thermometer socket and addition funnel, aluminium chloride (110 gms) and diethyl amine (61 gms) were charged at temperature 25° C. to 35° C. The reaction mass was heated to 100° C. to 105° C. and stirred for 30 minutes and then resveratrol methyl ether solution (25 gms of resveratrol methyl ether in 100 ml of toluene) was added at 100° C. to 110° C. Reaction mass was stirred for 7 hours at 110° C. to 115° C. and then allowed to cool to 65° C. to 75° C. The reaction mass was quenched into chilled water (350 ml) and stirred for 30 minutes at 25° C. to 35° C. Precipitated material was filtered and washed with water (50 ml). The wet product was slurred in hot water at 40° C. to 45° C. for 30 minutes and filtered. The wet product was dried at 70° C. to 80° C. for 4 hours under vacuum to provide the title compound as crude. The crude compound was dissolved in ethyl acetate (150 ml) at 40° C. to 45° C. and washed with aqueous HCl solution (15 ml of con HCl+60 ml of water) and then with water (70 ml). Layers were separated and distilled out the ethyl acetate under vacuum to obtain residue. The resultant residue was dissolved in methanol (140 ml) at 40° C. to 45° C. and then water (450 ml) was added at 25° C. to 35° C. Precipitated solids was filtered and washed with 10% methanol-water (15 ml). The wet product was dried at 70° C. to 80° C. under vacuum for 4 hours to provide the title compound.

Yield: 11.8 gms
HPLC Purity: 97.8%

Example 6

Preparation of Resveratrol Using Di-n-Propylamine: Aluminium Chloride

To a clean 3-necked 2 L round bottom flask equipped with a mechanical stirrer, thermometer socket and addition funnel, aluminium chloride (110 gms) and di-n-propylamine (85 gms) were charged at temperature 25° C. to 35° C. The reaction mass was heated to 110° C. to 120° C. and stirred for 30 minutes and then resveratrol methyl ether solution (25 gms of resveratrol methyl ether in 100 ml of toluene) was added at 110° C. to 115° C. Reaction mass was stirred for 6 hours at same temperature and then allowed to cool to 60° C. to 70° C. The reaction mass was quenched into chilled water (350 ml) and stirred for 30 minutes at 25° C. to 35° C. Precipitated material was filtered and washed with water (50 ml). The wet product was slurred in hot water at 40° C. to 45° C. for 30 minutes and filtered. The wet product was dried at 70° C. to 80° C. for 4 hours under vacuum to provide the title compound as crude. The crude compound was dissolved in ethyl acetate (150 ml) at 40° C. to 45° C. and washed with aqueous HCl solution (15 ml of con HCl+60 ml of water) and then with water (70 ml). Layers were separated and distilled out the ethyl acetate under vacuum to obtain residue. The resultant residue was dissolved in methanol (140 ml) at 40° C. to 45° C. and then water (450 ml) was added, at 25° C. to 35° C. Precipitated solids was filtered and washed with 10% methanol-water (15 ml). The wet product was dried at 70° C. to 80° C. under vacuum for 4 hours to provide the title compound.

Yield: 11.6 gms
HPLC Purity: 99.1%

Example 7

Preparation of Resveratrol Using Dicyclohexyl Amine: Aluminium Chloride

To a clean 3-necked 2 L round bottom flask equipped with a mechanical stirrer, thermometer socket and addition funnel, aluminium chloride (75 gms) and dicyclohexylmaine (100 gms) were charged at temperature 25° C. to 35° C. The reaction mass was heated to 110° C. to 120° C. and stirred for 60 minutes and then resveratrol methyl ether solution (25 gms of resveratrol methyl ether in 100 ml of toluene) was added at 100° C. to 110° C. Reaction mass was stirred for 2 hours at 110° C. to 115° C. and then allowed to cool to 100° C. to 110° C. The reaction mass was quenched into chilled water (350 ml) and stirred for 30 minutes at 25° C. to 35° C. Precipitated material was filtered and washed with water (50 ml). The wet product was slurred in hot water at 40° C. to 45° C. for 30 minutes and filtered. The wet product was dried at 70° C. to 75° C. for 4 hours under vacuum to provide the title compound as crude. The crude compound was dissolved in ethyl acetate (250 ml) at 40° C. to 45° C. and washed with aqueous HCl solution (25 ml of HCl+100 ml of water) and then with water (125 ml). Layers were separated and distilled out the ethyl acetate under vacuum to obtain residue. The residue was dissolved in methanol (70 ml) at 40° C. to 45° C. and then water (210 ml) was added at 25° C. to 35° C. Precipitated solids was filtered and washed with 10% methanol-water (10 ml). The wet product was dried at 70° C. to 80° C. under vacuum for 4 hours to provide the title compound.

Yield: 6 gms
HPLC Purity: 98.7%.

Example 8

Preparation of Resveratrol Using Di(2-Ethylhexyl)Amine: Aluminium Chloride

To a clean 3-necked 2 L round bottom flask equipped with a mechanical stirrer, thermometer socket and addition funnel aluminium chloride (75 gms) and di(2-ethylhexyl) amine (135 gms) were charged at temperature 25° C. to 35° C. The reaction mass was heated to 110° C. to 120° C. and stirred for 30 minutes and then resveratrol methyl ether solution (25 gms of resveratrol methyl ether in 100 ml of toluene) was added at 100° C. to 110° C. Reaction mass was stirred for 5 hours at 110° C. to 120° C. and then cooled to 60° C. to 70° C. The reaction mass was quenched into chilled water (350 ml) and stirred for 30 minutes at 25° C. to 35° C. Extracted the product with ethyl acetate (3×50 ml) and washed with aqueous HCl (25 ml HCl+100 ml water). Layers were separated and washed the organic layer with water (50 ml). The organic layer was distilled completely under vacuum and purified the resultant residue by column chromatography.

Eluents: 50% ethyl acetate in hexane.
Yield: 9.1 gms
HPLC Purity: 98.2%

Example 9

Preparation of Resveratrol Using Di-Isobutylamine: Aluminium Chloride

To a clean 3-necked 2 L round bottom flask equipped with a mechanical stirrer, thermometer socket and addition funnel, aluminium chloride (110 gms) and di-isobutylamine (108 gms) were charged at temperature 25° C. to 35° C. The reaction mass heated to 110° C. to 115° C. and stirred for 30 minutes and then resveratrol methyl ether solution (25 gms of resveratrol methyl ether in 100 ml of toluene) was added at 100° C. to 110° C. Reaction mass was stirred for 4 hours at 110° C. to 115° C. and then cooled to 65° C. to 70° C. The reaction mass was quenched into chilled water (350 ml) and stirred for 30 minutes at 25° C. to 30° C. Extracted the product with ethyl acetate (375 ml) and washed with aqueous HCl (25 ml HCl+75 ml water). Layers were separated and washed the organic layer with water (50 ml). The organic layer was distilled completely under vacuum to obtain residue. The residue was dissolved in methanol (170 ml) at 40° C. to 45° C. and then water (540 ml) was added at 25° C. to 35° C. Precipitated product was filtered and washed with 10% methanol-water (20 ml). The wet product was dried at 70° to 80° C. for 4 hours under vacuum to provide the title compound.

Yield: 13.5 gms
HPLC Purity: 99.1%

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparing polyhydroxy stilbenes of Formula I or its isomers thereof:

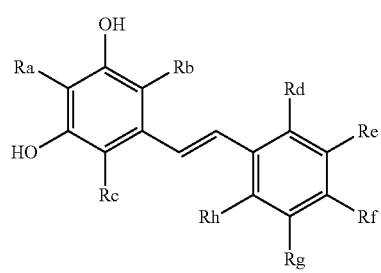

Formula I wherein
Rd, Rf, Ku and Rh are independently hydrogen or a OH group;
Ra, Rb, Re, and Re are independently a hydrogen, a halogen, a nitro group, a linear or branched $C_1$-$C_4$ alkyl group, a linear or branched $C_2$-$C_6$ alkenyl group, a $C_3$-$C_{10}$ cycloalkyl group; a cycloalkylalkyl group in which the cycloalkyl is $C_3$-$C_{10}$ cycloalkyl and the alkyl is $C_1$-$C_4$ alkyl; an aryl group; or an aralkyl group;
the process comprising the step of deprotecting a compound of Formula II or its isomers thereof using an aluminum halide and a secondary amine

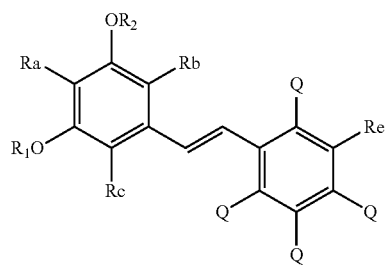

Formula II wherein
Ra, Rb, Rc and Re are defined as above;
Q is hydrogen or an $OR_i$ group; and
$R_1$, $R_2$ and $R_i$ are independently a linear or branched $C_1$-$C_4$ alkyl group; a C(=O)$R_j$, wherein $R_j$ is a linear or branched $C_1$-$C_4$ alkyl group; or an aralkyl group, wherein an aryl portion in the aralkyl group is optionally substituted by one or more $C_1$-$C_4$ alkoxy or halogen groups.

2. The process of claim 1, wherein Ra, Rb, Rc and Re are independently hydrogen, and one of Rd, Rf, Rg and Rh is hydrogen or a OH group.

3. The process of claim 1, wherein Ra, Rb, Rc, and Re are independently hydrogen.

4. The process of claim 1, wherein $R_1$, $R_2$ and $R_i$ are independently a linear or branched $C_1$-$C_4$ alkyl group; or an aralkyl group, wherein an aryl portion in the aralkyl group is optionally substituted by one or more $C_1$-$C_4$ alkoxy or halogen groups.

5. The process of claim 4, wherein $R_1$, $R_2$ and $R_i$ are independently methyl, ethyl, t-butyl or benzyl group.

6. The process of claim 1, wherein the aluminum halide is selected from the group consisting of aluminum chloride, aluminum bromide, and aluminum iodide.

7. The process of claim 6, wherein the aluminum halide is aluminum chloride.

8. The process of claim 1, wherein the secondary amine is of Formula (R)$_2$NH, wherein R is a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, or an aralkyl group.

9. The process of claim 8, wherein the secondary amine of Formula (R)$_2$NH is selected from the group consisting of diemylamine, diisopropyl amine, di-n-propylamine, diisobutylarnine, diallylamine, allylmethyl amine, diphenylamine, dibenzylamine, benzylethyl amine, methylbenzyl amine, dicyclohexylamine, N-t-butyl cyclohexylamine, N-isobutyl cyclohexylamine, di(2-ethylhexyl)amine, and dicyclohexylmethyl amine.

10. The process of claim 8, wherein the secondary amine of Formula (R)$_2$NH is selected from the group comprising diisopropyl amine, diethylamine, di-n-propylamine, diisobutylarnine, dicyclohexylamine, and di(2-ethylhexyl)amine.

11. The process of claim 1, wherein the deprotecting step is carried out in the presence of a solvent.

12. The process of claim 11, wherein the solvent is a halogenated hydrocarbon selected from the group consisting of dichloromethane, dichloroethane, and chloroform; an aromatic hydrocarbon selected from the group consisting of toluene, xylene, chlorobenzene, and 1,2-dichlorobenzene; diphenyl ether; or mixtures thereof.

13. The process of claim 11, wherein the solvent is toluene.

14. The process of claim 1, wherein the deprotecting step is carried out at a temperature of ambient temperature to about reflux temperature.

15. The process of claim 14, wherein the temperature is about 80° C. to about 120° C.

16. A process for preparing resveratrol of the formula

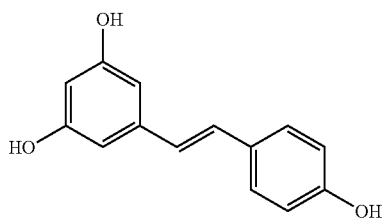 [SMILES: Oc1ccc(/C=C/c2cc(O)cc(O)c2)cc1]

or its isomers thereof, the process comprising the step of deprotecting a resveratrol ether compound

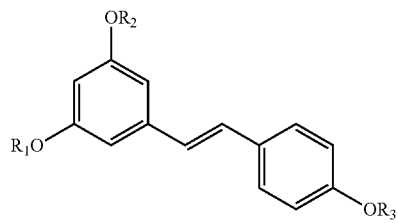

or its isomers thereof,
wherein $R_1$, $R_2$ and $R_3$ are independently a methyl, and
wherein the deprotecting step is carried out with use of an aluminum halide, and a secondary amine of Formula $(R)_2NH$, wherein R is a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, or an aralkyl group.

17. The process of claim 16, wherein the aluminum halide is aluminum chloride.

18. The process of claim 16, wherein the secondary amine of Formula $(R)_2NH$ is selected from the group consisting of diisopropyl amine, diemylamine, di-n-propylamine, diisobutylamine, dicyclohexylamine, and di(2-ethylhexyl)amine.

19. The process of claim 16, wherein the deprotecting step is carried out in the presence of a solvent.

20. The process of claim 19, wherein the solvent is toluene.

* * * * *